(12) United States Patent
Jin et al.

(10) Patent No.: US 11,793,852 B2
(45) Date of Patent: Oct. 24, 2023

(54) APPLICATION OF LONGHU RENDAN IN PREPARING MEDICAMENT FOR PREVENTING AND/OR TREATING LIVER FIBROSIS

(71) Applicant: Shanghai Zhonghua Pharmaceutical Co., Ltd, Shanghai (CN)

(72) Inventors: Jiahua Jin, Shanghai (CN); Biye Wang, Shanghai (CN); Liqin Ding, Shanghai (CN); Wujie Cao, Shanghai (CN); Xiaoping Zhu, Shanghai (CN); Tian Lan, Guangdong (CN)

(73) Assignee: Shanghai Zhonghua Pharmaceutical Co., Ltd, Shanghai (CN)

( * ) Notice: Subject to any disclaimer, the term of this patent is extended or adjusted under 35 U.S.C. 154(b) by 404 days.

(21) Appl. No.: 17/079,524

(22) Filed: Oct. 26, 2020

(65) Prior Publication Data

US 2021/0038675 A1    Feb. 11, 2021

Related U.S. Application Data

(63) Continuation of application No. 16/319,305, filed as application No. PCT/CN2018/084010 on Apr. 23, 2018, now abandoned.

(30) Foreign Application Priority Data

May 2, 2017   (CN) .......................... 201710301074.2

(51) Int. Cl.
| | | |
|---|---|---|
| A61K 36/9068 | (2006.01) |
| A61P 1/16 | (2006.01) |
| A61K 31/045 | (2006.01) |
| A61K 36/28 | (2006.01) |
| A61K 36/484 | (2006.01) |
| A61K 36/534 | (2006.01) |
| A61K 36/54 | (2006.01) |
| A61K 36/61 | (2006.01) |
| A61K 36/67 | (2006.01) |
| A61K 36/79 | (2006.01) |
| A61K 36/899 | (2006.01) |
| A61K 36/9064 | (2006.01) |
| A61K 47/02 | (2006.01) |
| A61K 47/12 | (2006.01) |
| A61K 47/34 | (2017.01) |
| A61K 47/36 | (2006.01) |
| A61K 36/285 | (2006.01) |
| A61K 36/48 | (2006.01) |
| A61K 36/57 | (2006.01) |

(52) U.S. Cl.
CPC ........ *A61K 36/9068* (2013.01); *A61K 31/045* (2013.01); *A61K 36/28* (2013.01); *A61K 36/285* (2013.01); *A61K 36/48* (2013.01); *A61K 36/484* (2013.01); *A61K 36/534* (2013.01); *A61K 36/54* (2013.01); *A61K 36/57* (2013.01); *A61K 36/61* (2013.01); *A61K 36/67* (2013.01); *A61K 36/79* (2013.01); *A61K 36/899* (2013.01); *A61K 36/9064* (2013.01); *A61K 47/02* (2013.01); *A61K 47/12* (2013.01); *A61K 47/34* (2013.01); *A61K 47/36* (2013.01); *A61P 1/16* (2018.01)

(58) Field of Classification Search
CPC .. A61K 36/9068; A61K 31/045; A61K 36/28; A61K 36/285; A61K 36/48; A61K 36/484; A61K 36/534; A61K 36/54; A61K 36/57; A61K 36/61; A61K 36/67; A61K 36/79; A61K 36/899; A61K 36/9064; A61K 47/02; A61K 47/12; A61K 47/34; A61K 47/36; A61K 9/2059; A61P 1/16
See application file for complete search history.

(56) References Cited

FOREIGN PATENT DOCUMENTS

CN    101637607 A   *   2/2010

* cited by examiner

Primary Examiner — Aaron J Kosar
(74) Attorney, Agent, or Firm — JCIPRNET

(57) ABSTRACT

An application of Longhu Rendan in preparing a medicament for preventing and/or treating liver fibrosis. The Longhu Rendan has significant effect in improving fibrosis, and its effect in anti-liver fibrosis and liver protection is equivalent to those of a positive drug silybin.

2 Claims, 4 Drawing Sheets

APPLICATION OF LONGHU RENDAN IN PREPARING MEDICAMENT FOR PREVENTING AND/OR TREATING LIVER FIBROSIS

CROSS-REFERENCE TO RELATED APPLICATIONS

This application is a continuation application of U.S. application Ser. No. 16/319,305, filed on Jan. 18, 2019, now pending. The U.S. application Ser. No. 16/319,305 is a 371 of International PCT Application serial no. PCT/CN2018/084010, filed on Apr. 23, 2018, which claims the priority benefit of China application no. 201710301074.2, filed on May 2, 2017. The entirety of each of the above-mentioned patent applications is hereby incorporated by reference herein and made a part of this specification.

BACKGROUND OF THE INVENTION

1. Field of the Invention

The present invention relates to preparation of medicaments for liver fibrosis, and in particular, application of Longhu Rendan in the preparation of a medicament for preventing and/or treating liver fibrosis.

2. Description of Related Art

Liver fibrosis is a ubiquitous injury repair response in various chronic liver injury processes, and its main feature is the massive deposition of extracellular matrix (ECM). If liver fibrosis is not treated in time, it eventually develops into cirrhosis. In addition, liver fibrosis is also considered to be an important cause of liver cancer. Liver fibrosis can be reversed by timely and rational intervention. At present, there is no effective therapeutic agent for treatment of liver fibrosis. Liver fibrosis is usually treated with chemical drugs, but chemotherapy has low safety, high toxicity, and high cost, as well as a large side effect on the human body. Therefore, it has become a hot research topic at home and abroad to find an effective agent for treating liver fibrosis.

SUMMARY OF THE INVENTION

It is an object of the present invention to provide application of Longhu Rendan in the preparation of a medicament for preventing and/or treating liver fibrosis. Longhu Rendan in the present invention can significantly improve fibrosis, and has anti-liver fibrosis and liver protection effects that are equivalent to those of a positive drug silybin.

The present invention provides application of Longhu Rendan in the preparation of a medicament for preventing and/or treating liver fibrosis.

Preferably, Longhu Rendan comprises the following components in the following parts by mass per 1000 g: 32 to 48 g of menthol, 24 to 36 g of borneol, 20 to 30 g of clove, 20 to 30 g of *fructus amomi*, 12 to 18 g of star anise, 32 to 48 g of cinnamon, 12 to 18 g of pepper, 12 to 18 g of costus root, 20 to 30 g of dried ginger, 160 to 240 g of *catechu*, 291.28 to 436.92 g of licorice, 144 to 216 g of glutinous rice flour, 4 to 6 g of sodium benzoate, 11.6 to 17.4 g of red iron oxide, 0.08 to 0.12 ml of dimethicone, 0.16 to 0.24 g of graphite, 0.16 to 0.24 g of talc, and 3.16 to 4.74 g of dextrin.

Preferably, the formulation of Longhu Rendan comprises tablets, powders, granules, pills, and capsules.

Preferably, an effective dose of Longhu Rendan is 100 mg/kg to 200 mg/kg.

The present invention provides application of Longhu Rendan in the preparation of a medicament for preventing and/or treating liver fibrosis. In the present invention, Longhu Rendan can significantly improve fibrosis, and has anti-liver fibrosis and liver protection effects that are equivalent to those of a positive drug silybin. Also, Longhu Rendan has fewer side effects and higher safety. The test results show that, Longhu Rendan at low and medium drug concentrations can significantly improve fibrosis, and has anti-liver fibrosis and liver protection effects that are equivalent to those of a positive drug silybin.

DESCRIPTION OF THE DRAWINGS

FIG. 1A shows the results of serum AST activity in mice and FIG. 1B shows the results of serum ALT activity in mice.

FIG. 2A shows the results of HE staining of mouse livers, FIG. 2B shows the results of Sirius Red staining of mouse livers, and FIG. 2C shows the results of α-SMA immunohistochemical staining of mouse livers.

DETAILED DESCRIPTION OF THE INVENTION

Figure 1B:
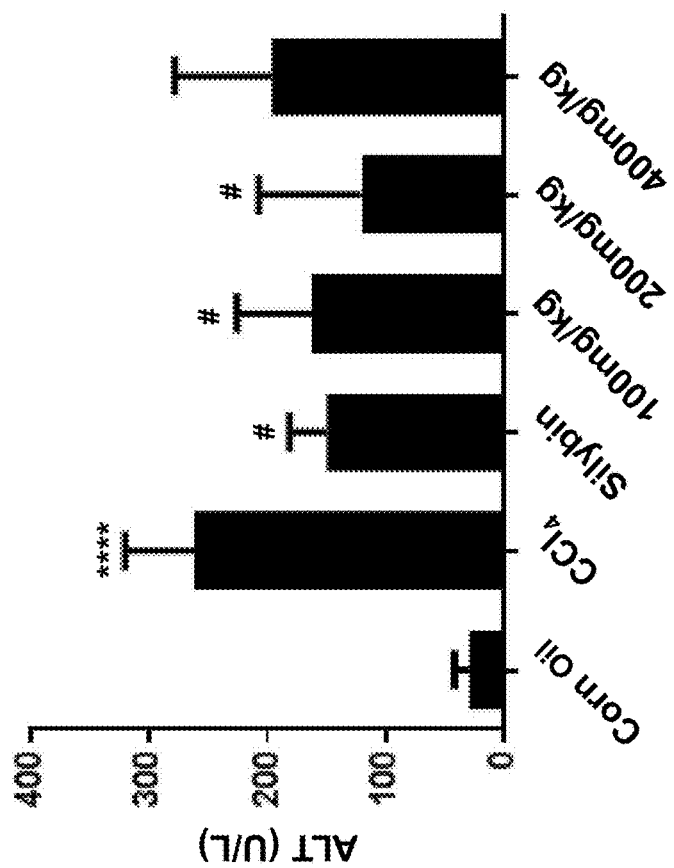
FIGS. 1A and 1B are diagrams showing the effect of Longhu Rendan provided in Example 1 of the present invention on serological indicators in mice with liver fibrosis induced by $CCl_4$, where

The present invention provides application of Longhu Rendan in the preparation of a medicament for preventing and/or treating liver fibrosis.

In the present invention, Longhu Rendan comprises the following components in the following parts by mass per 1000 g: 32 to 48 g of menthol, 24 to 36 g of borneol, 20 to 30 g of clove, 20 to 30 g of *fructus amomi*, 12 to 18 g of star anise, 32 to 48 g of cinnamon, 12 to 18 g pepper, 12 to 18 g of costus root, 20 to 30 g of dried ginger, 160 to 240 g of *catechu*, 291.28 to 436.92 g of licorice, 144 to 216 g of glutinous rice flour, 4 to 6 g of sodium benzoate, 11.6 to 17.4 g of red iron oxide, 0.08 to 0.12 ml of dimethicone, 0.16 to 0.24 g of graphite, 0.16 to 0.24 g of talc, and 3.16 to 4.74 g of dextrin. In the present invention, the source of Longhu Rendan is not particularly limited, as long as commercial products of Longhu Rendan well-known to those skilled in the art are used, for example, Longhu Rendan sold by Shanghai Zhonghua Pharmaceutical Co., Ltd. Common effects of Longhu Rendan of the present invention in the prior art include resuscitation and refreshment, dampness-removing and turbid-expelling, and center-warming and vomiting-arresting, as well as spleen and stomach regulating, and turbid vanishing and transport increasing; and in the present invention, Longhu Rendan can achieve prevention and/or treatment of liver fibrosis.

In the present invention, the formulation of Longhu Rendan comprises tablets, powders, granules, pills, and capsules.

In the present invention, an effective dose of Longhu Rendan is 100 mg/kg to 200 mg/kg.

In the present invention, a dilution agent is included in the application of Longhu Rendan. The dilution agent is not particularly limited, as long as a medicament carrier well-known to those skilled in the art are used, for example, sodium hydroxymethyl cellulose (CMC-Na). In the present invention, the concentration by mass of sodium hydroxymethyl cellulose in Longhu Rendan is preferably 0.5%. In the present invention, the dilution agent is used to ensure the amount of administration, and in the present invention, the administration is done preferably by gastric perfusion. In the present invention, the dilution agent sodium hydroxymethyl cellulose has no significant effect on fibrosis, only serves as a common suspending agent in medicaments, belongs to an inert molecule, and has no obvious biological activity.

In the present invention, the preparation method of Longhu Rendan is not particularly limited, as long as preparation methods of commercial products of Longhu Rendan well-known to those skilled in the art are used. For example, the preparation method may refer to the limitations of a preparation method in Chinese Patent Application No. 200910194559.1, and specifically comprises the following steps: (1) preparation of soft material: a. formulation of *catechu* slurry: *catechu* and purified water are mixed with stirring per the above parts by mass in a mass ratio of 1:1 while controlling a steam pressure of 0.25 to 0.5 Mpa and a temperature of 60 to 95° C., heated to be dissolved, and filtered to give a *catechu* solution; then, sodium benzoate, the *catechu* solution, and 5 to 18% of the above amount of glutinous rice flour are stirred by portions for 3 to 5 min, slurried for 10 to 30 min, and discharged; b. preparation of mixed powder: glutinous rice flour, *fructus amomi* powder, star anise powder, cinnamon powder, pepper powder, costus root powder, dried ginger powder, clove powder, and licorice powder are dosed in mixture in the above parts by mass, and volatile raw materials previously melt and filtered are sprayed thereto with stirring, and discharged after completion of the spraying; c. the mixed powder and the *catechu* slurry are mixed with stirring for 15 to 30 min and discharged; (2) preparation of pills: a. the soft material is made into wet rough pills that are rounded in shape and uniform in size; b. the wet rough pills are polished, stirred uniformly with addition of the dextrin solution, blown, and rolled to generate a glossy surface, red iron oxide is applied thereto, and dimethicone is dropped therein, and the coating time is 0.5 to 2.5 h; and c. the pills are dried and sterilized, and the pills having a diameter of 4.0 mm to 4.5 mm are selected, and polished with addition of graphite powder and talc powder.

The application of Longhu Rendan in the preparation of a medicament for preventing and/or treating liver fibrosis according to the present invention is further described in detail below in conjunction with specific examples, and the technical solution of the present invention includes, but is not limited to, the following examples.

Example 1

Experimental animals: SPF grade C57 mice, 8-week old, half male and half female, supplied by Guangdong Medical Lab Animal Center, housed in an animal room in a barrier environment (SPF grade), and feeds and water ad libitum. Certificate [SCXK(YUE) 2013-0002].

The experimental agents and reagents used in the experiment are shown in Table 1:

TABLE 1

| Experimental agents and reagents | | |
|---|---|---|
| Material | Lot number | Manufacturer |
| Sodium carboxymethylcellulose | C830BA0009 | Sangon Biotech (Shanghai) Co., Ltd. |
| Longhu Rendan | 160108 | Shanghai Zhonghua Pharmaceutical Co., Ltd. |
| Silybin capsule | 550609055 | Tianjin Tianshili Shengte Pharmaceutical Co., Ltd. |
| $CCl_4$ | E1422028 | Aladdin |

The experimental apparatuses are shown in Table 2:

TABLE 2

| Experimental apparatuses | | |
|---|---|---|
| Apparatus | Model | Manufacturer |
| Electronic balance | B604028467 | Mettler-Toledo Instruments (Shanghai) Co., Ltd. |
| Photomicroscope | X51 | Olympus |
| Ultra-clean workbench | BCM-1000 | Suzhou Antai (China) |

Experimental Design

Administration: 32 pills of Longhu Rendan were placed in a mortar and ground, dissolved in 20 mL of 0.5% CMC-Na, pipetted into a 50-mL centrifuge tube, vortexed to be completely dissolved, and made up to 32 mL (solution A). Six 5-ml EP tubes were charged with the solution A per 3 mL/tube (namely, daily dosage for a high-dose group). Another 50-mL tube was charged with 9 ml of the solution A, added with 9 mL 0.5% CMC-Na, and mixed uniformly; and six 5-ml EP tubes were charged with the solution per 3 mL/tube (namely, daily dosage for a medium-dose group). Another 50-mL centrifuge tube was charged with 4.5 ml of the solution A, added with the 0.5% CMC-Na solution to 18 mL, and mixed uniformly; and six 5-ml EP tubes were charged with the solution per 3 mL/tube (namely, daily dosage for a low-dose group). Continue for 6 weeks, 6×32 pills=192 pills in total, about 4 boxes.

Formulation of silybin: one 50-mL centrifuge tube was added with 10 to 12 mL of 0.5% CMC-Na, charged with 4 capsules, dissolved, made up to 20 mL with 0.5% CMC-Na, and mixed uniformly. Six 5-ml EP tubes were charged with the solution per 3 mL/tube (namely, daily dosage). Continue for 6 weeks, 6×4 capsules=24 capsules in total, about 2 boxes.

Modeling, Grouping and Administration Methods 60 healthy KM mice were randomly divided into 6 groups with 8 mice/group. Namely: a blank control group, a $CCl_4$ model group, a silybin positive control group, and low, medium, and high dose groups of Longhu Rendan. All groups received a normal diet. The blank control group and the $CCl_4$ model group were administered with an equal volume of 0.5% CMC-Na once daily by gastric perfusion, the silybin group was administered at a dosage of 70 mg/kg/d, and the mice in the experimental groups were administered with Longhu Rendan at 100 mg/kg/d for the low-dose group, 200 mg/kg/d for the medium-dose group, and 400 mg/kg/d for the high dose group, once daily, for 6 consecutive weeks.

Serological Indicators:

After fasting for 12 h, the eyeballs were removed and blood was taken and serum was separated. ALT and AST activities were determined by alanine aminotransferase (ALT) and aspartate aminotransferase (AST) kits.

Figure 1A:
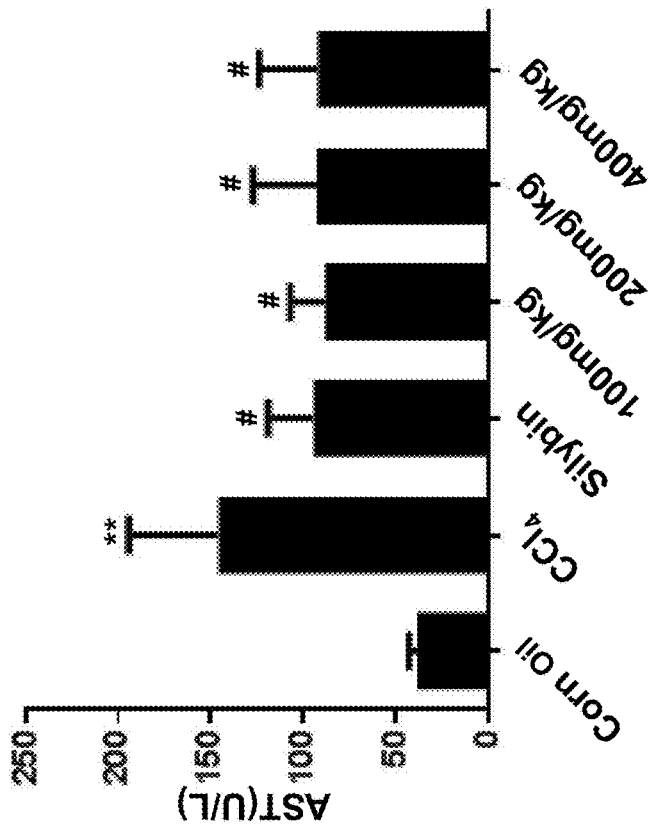

FIGS. 1A and 1B are diagrams showing the effect of Longhu Rendan on serological indicators in mice with liver fibrosis induced by $CCl_4$, where FIG. 1A shows the results of serum AST activity in mice and FIG. 1B shows the results of serum ALT activity in mice. The results of FIGS. 1A and 1B show that compared to the $CCl_4$ group, ASTs in the positive drug silybin and the three doses of groups of Longhu Rendan are all significantly reduced (P<0.05), and ALTs in the low-dose group and the medium-dose group are all significantly reduced (P<0.05) in spite of no improvement in the high-dose group of 400 mg/kg.

Pathological Indicators:

HE staining, Sirius Red staining, and smooth muscle actin protein α-SMA immunohistochemical staining. Positive staining areas of Sirius Red staining and immunohistochemical staining were calculated by the ImageJ software, data was processed and plotted by GraphPadPrism, and t-test analysis was performed, where P<0.05 was considered statistically significant.

Figure 2A:
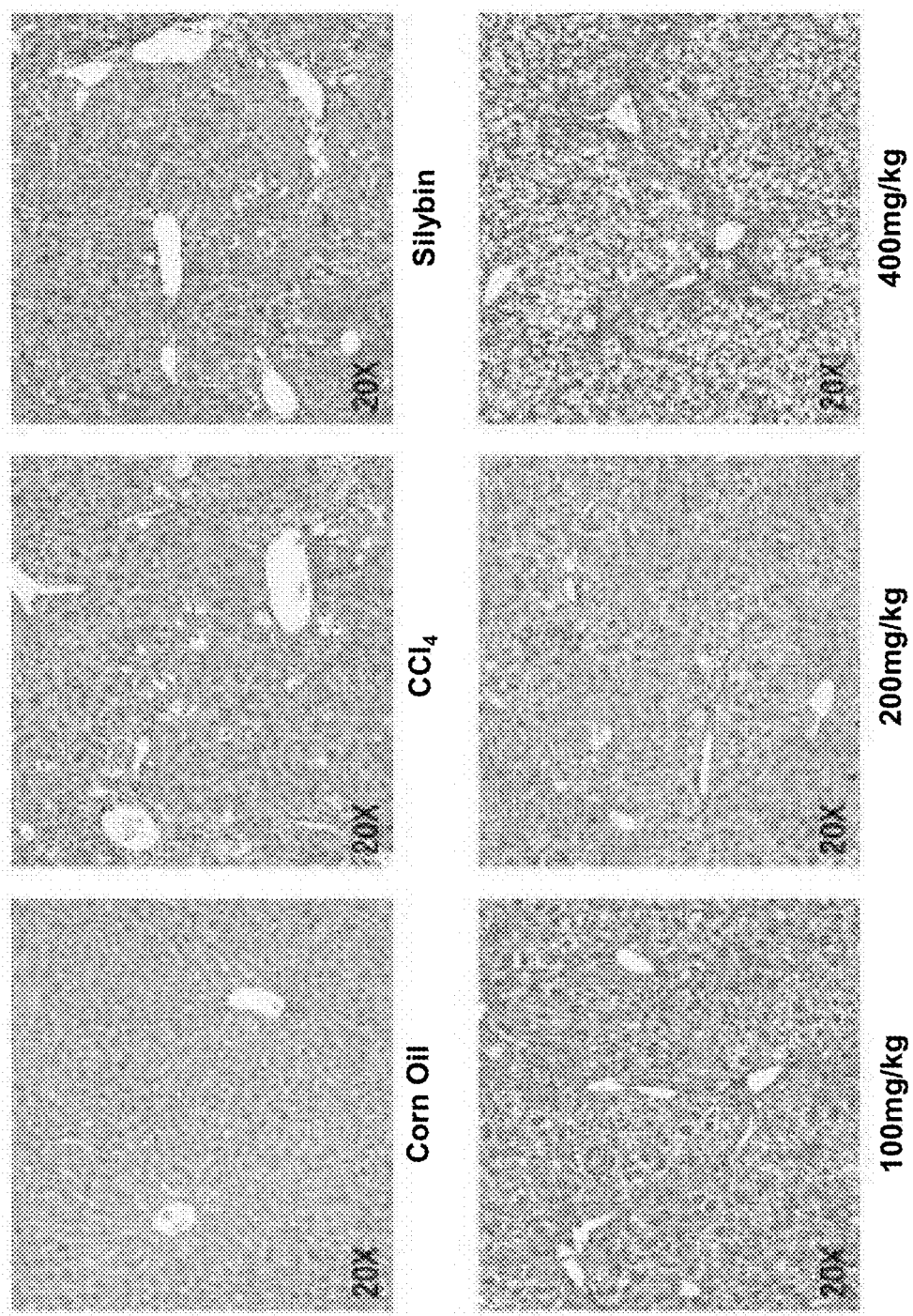
FIGS. 2A, 2B and 2C are diagrams showing the effect of Longhu Rendan provided in Example 1 of the present invention on pathological indicators in mice with liver fibrosis induced by $CCl_4$, where
Figure 2B:
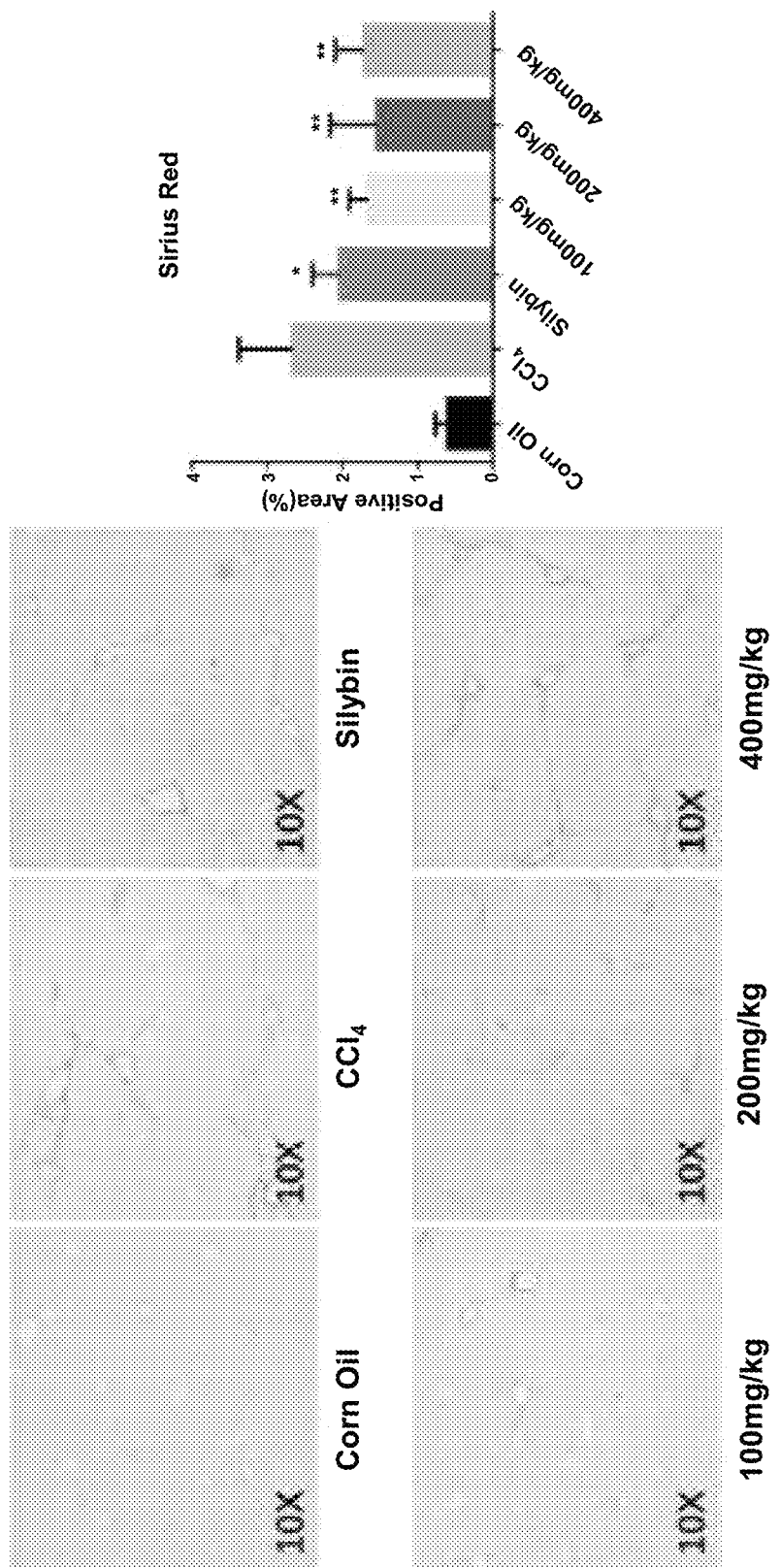
Figure 2C:
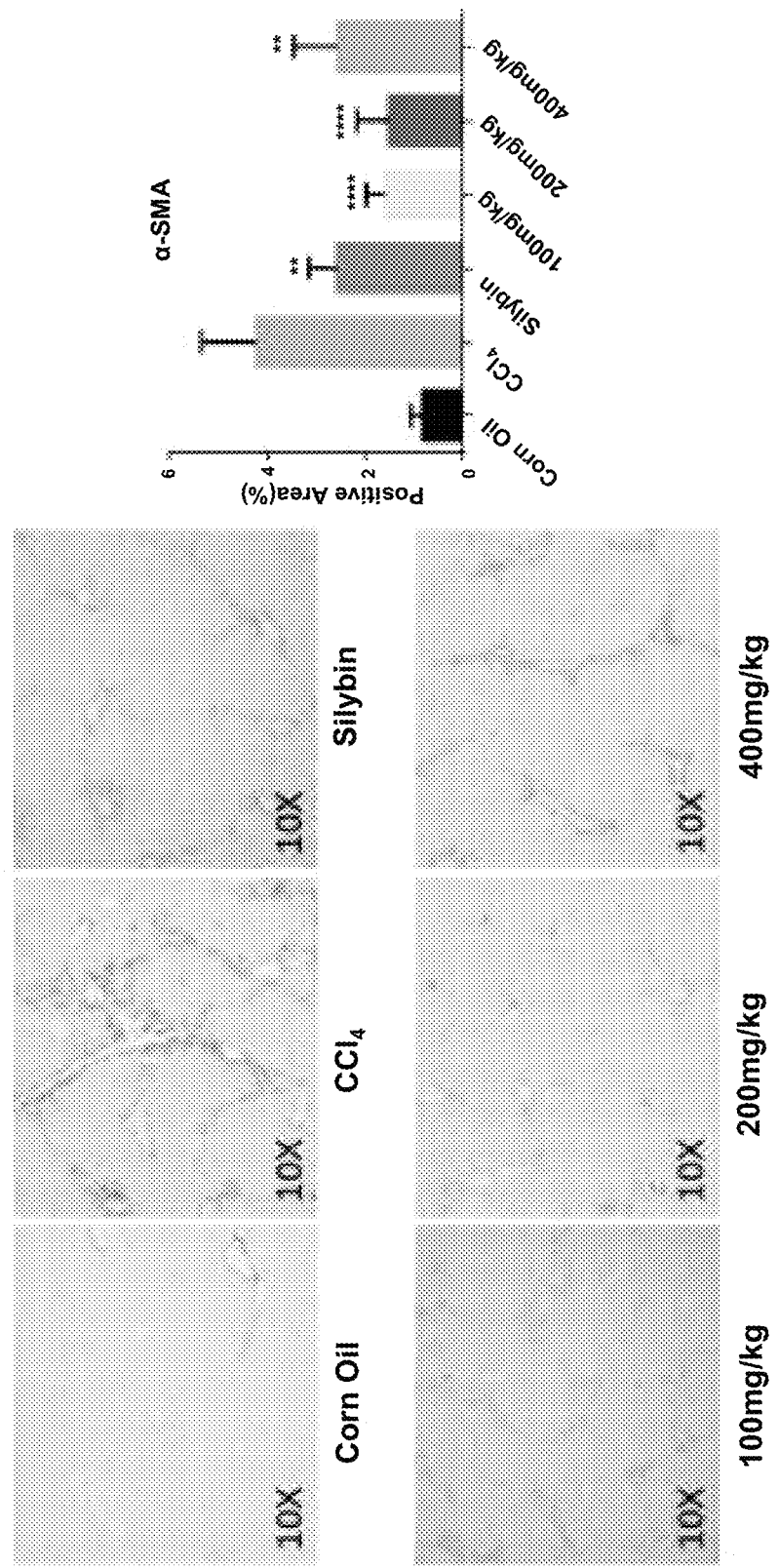

Firstly, HE staining was performed on mouse liver slices, and general morphology was observed. FIGS. 2A, 2B and 2C are diagrams showing the effect of Longhu Rendan on pathological indicators in mice with liver fibrosis induced by $CCl_4$, where FIG. 2A shows the results of HE staining of mouse livers, FIG. 2B shows the results of Sirius Red staining of mouse livers, and FIG. 2C shows the results of α-SMA immunohistochemical staining of mouse livers. It can be seen from FIG. 2A that compared to the Corn Oil group, the $CCl_4$ group has significant inflammatory infiltration and liver injury; compared to the $CCl_4$ model group, the silybin group and the three doses of groups of Longhu Rendan are improved at different degrees in inflammatory infiltration and liver injury, where improvement is more significant at 100 mg/kg and 200 mg/kg. Then, Sirius Red staining (FIG. 2B) and immunohistochemical staining (α-SMA) (FIG. 2C) were performed, and it was also observed that the silybin group and the three doses of groups of Longhu Rendan all could significantly improve the degree of fibrosis in the mice.

Longhu Rendan at low and medium drug concentrations (100 mg/kg and 200 mg/kg) can significantly improve fibrosis, and has anti-liver fibrosis and liver protection effects that are equivalent to those of the positive drug silybin. When the drug concentration is too high, the liver protection and anti-liver fibrosis effects are reduced, possibly due to instability of the pharmaceutical preparation system or gastrointestinal irritation or poor drug absorption, etc.

The description above merely gives the preferred embodiments of the present invention. It should be noted that several modifications and variations can be made by those of ordinary skill in the art without departing from the principles of the invention, and these modifications and variations should be considered within the scope of the present invention.

What is claimed is:

1. A method for preventing and/or treating liver fibrosis, comprising administration of a medicament,
    wherein the medicament comprises following components in parts by mass: 32 g to 48 g of menthol, 24 g to 36 g of borneol, 20 g to 30 g of clove, 20 g to 30 g of fructus amomi, 12 g to 18 g of star anise, 32 g to 48 g of cinnamon, 12 g to 18 g of pepper, 12 g to 18 g of costus root, 20 g to 30 g of dried ginger, 160 g to 240 g of *catechu*, 291.28 g to 436.92 g of licorice, 144 g to 216 g of glutinous rice flour, 4 g to 6 g of sodium benzoate, 11.6 g to 17.4 g red iron oxide, 0.08 ml to 0.12 ml of dimethicone, 0.16 g to 0.24 g of graphite, 0.16 g to 0.24 g of talc, and 3.16 g to 4.74 g of dextrin in every 1000 g, and
    wherein an effective dose of the medicament is 100 mg/kg to 200 mg/kg.

2. The method for preventing and/or treating liver fibrosis of claim 1, wherein a formulation of the medicament comprises tablets, powders, granules, pills, and capsules.

* * * * *